United States Patent [19]

Iwata et al.

[11] Patent Number: 5,028,716
[45] Date of Patent: Jul. 2, 1991

[54] 3,5-DIAMINO-1,2,4-TRIAZOLE DERIVATIVES

[75] Inventors: Chuzo Iwata, Settsu; Takeshi Imanishi, Nara; Yoshiyuki Chiba; Mikio Satake, both of Hachioji; Masakazu Sato, Konosu; Yutaka Kawashima, Tatebayashi; Jun Goto, Omiya, all of Japan

[73] Assignees: Taisho Pharmaceutical Co., Ltd.; Nippon Suisan Kaisha, Ltd., both of Japan

[21] Appl. No.: 469,060

[22] Filed: Jan. 23, 1990

[30] Foreign Application Priority Data

Jan. 30, 1989 [JP] Japan ..................................... 1-20525

[51] Int. Cl.$^5$ ............................................. C07D 249/08
[52] U.S. Cl. ................................................ 548/265.2
[58] Field of Search ..................................... 548/265.2

[56] References Cited

FOREIGN PATENT DOCUMENTS

| | | |
|---|---|---|
| 030092 | 11/1980 | European Pat. Off. . |
| 0057564 | 1/1984 | European Pat. Off. . |
| 0177054 | 4/1985 | European Pat. Off. . |
| 2917026 | 4/1979 | Fed. Rep. of Germany . |
| 248589 | 8/1987 | German Democratic Rep. ............................... 548/265.2 |

OTHER PUBLICATIONS

*Chemical Abstracts*, vol. 108, No. 7, Feb. 15, 1988, p. 718, Col. 2, Ab. No. 55990b.
*Chemical Abstracts*, vol. 104, No. 19, May 12, 1986, p. 673, Col. 2, Ab. No. 168468y.
*Chemical Abstracts*, vol. 98, No. 3, Jan. 17, 1983, p. 15, Col. 1, Ab. No. 11101h.

Primary Examiner—Mary C. Lee
Assistant Examiner—Patricia L. Morris
Attorney, Agent, or Firm—Lorusso & Loud

[57] ABSTRACT

A triazole derivative represented by the formula

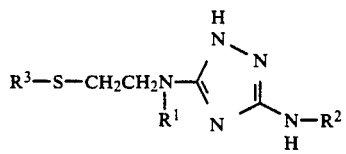

wherein $R^1$ is a hydrogen atom, a lower alkyl group having 1 to 4 carbon atoms, an acetyl group, a naphthylmethyl group, an anthrylmethyl group or a group of the formula

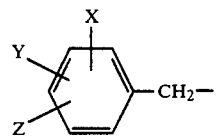

wherein X, Y and Z are the same or different and each a hydrogen atom, a halogen atom, a lower alkyl group having 1 to 4 carbon atoms, a lower alkoxy group having 1 to 4 carbon atoms, a hydroxyl group, a nitro group, a trifluoromethyl group, a cyano group or a benzyloxy group, and $R^2$ is a hydrogen atom or an acetyl group, and $R^3$ is a hydrogen atom, an acetyl group or a group of the formula

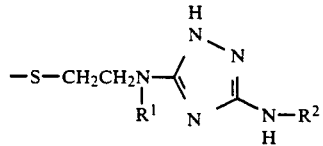

wherein $R^1$ and $R^2$ are as defined above, are useful as the inhibitors of lipid peroxidation.

11 Claims, No Drawings

3,5-DIAMINO-1,2,4-TRIAZOLE DERIVATIVES

BACKGROUND OF THE INVENTION (1) Field of the Invention

The present invention relates to triazole derivatives having the inhibiting activity of lipid peroxidation.

(2) Prior Art of the Invention

It is known that lipid peroxide has the property to induce denaturation of the membrane or the emzyme which causes the injury and function lowering of the cells, and has the property to involve with various diseases such as arteriosclerotic diseases including myocardial and cerebral infarctions, liver diseases, pulmonary edema, skin diseases and eye diseases, and ageing.

As the agents to inhibit lipid peroxidation, there are reported vinpocetine (Neuropsychic Pharmacology, vol. 7, page 113, 1985), idebenone (Pharmacology and Therapy, vol. 13, page 673, 1985) and the like. However, any compounds sufficient for its activity have not been found.

As a result of the earnest resarches on compounds having triazole skeleton, the present inventors have found novel triazole derivatives useful as the inhibitors of lipid peroxidation.

SUMMARY OF THE INVENTION

An object of the present invention is to provide a triazole derivative represented by the formula

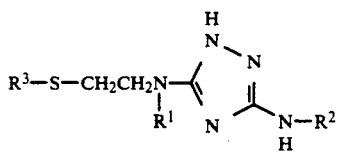

wherein $R^1$ is a hydrogen atom, a lower alkyl group having 1 to 4 carbon atoms, an acetyl group, a naphthylmethyl group, an anthrylmethyl group or a group of the formula

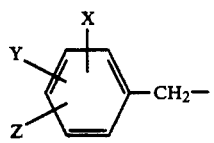

wherein X, Y and Z are the same or different and each a hydrogen atom, a halogen atom, a lower alkyl group having 1 to 4 carbon atoms, a lower alkoxy group having 1 to 4 carbon atoms, a hydroxyl group, a nitro group, a trifluoromethyl group, a cyano group or a benzyloxy group, and $R^2$ is a hydrogen atom or an acetyl group, and $R^3$ is a hydrogen atom, an acetyl group or a group of the formula

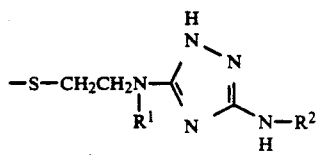

wherein $R^1$ and $R^2$ are as defined above.

In the present invention, the lower alkyl group having 1 to 4 carbon atoms refers to a straight or branched chain alkyl group such as a methyl group, an ethyl group, a propyl group, an isopropyl group, a butyl group, an isobutyl group and a t-butyl group. The lower alkoxy group having 1 to 4 carbon atoms refers to a straight or branched chain alkoxy group such as a methoxy group, an ethoxy group, a propoxy group, an isopropoxy group or a butoxy group. The halogen atom refers to a fluorine atom, a chlorine atom, a bromine atom or an iodine atom.

Preferred compounds of the present invention are 5-amino-3-[N-(2-mercaptoethyl)benzylamino]-1,2,4-triazole, 5-amino-3-[N-(2-mercaptoethyl)-2,4,6-trimethylbenzylamino]-1,2,4-triazole, bis{2-[N-(5-amino-1,2,4-triazol-3-yl)-N-benzylamino]ethyl}-disulfide, bis{2-[N-(5-amino-1,2,4-triazol-3-yl)-N-(3-bromobenzyl)amino]ethyl}disulfide, bis{2-[N-(5-amino-1,2,4-triazol-3-yl)-N-(4-benzyloxybenzyl)amino}-ethyl)disulfide, bis{2-[N-(5-amino-1,2,4-triazol-3-yl)-N-(2,5-dimethylbenzyl)amino]ethyl}disulfide, bis{2-[N-(5-amino-1,2,4-triazol-3 -yl)-N-(2,4,6-trimethylbenzyl)-amino]ethyl}disulfide, bis{2-[N-(5-amino-1,2,4-triazol-3-yl)-N-(4-tert-butylbenzyl)amino]ethyl}disulfide, bis{2-[N-(5-amino-1,2,4-triazol-3-yl)-N-(α-naphthylmethyl)amino]ethyl}disulfide, and bis{2-[N-(5-amino-1,2,4-triazol-3-yl)-N-(β-naphthylmethyl)amino]ethyl}disulfide.

DETAILED DESCRIPTION OF THE INVENTION

The compound of Formula I can be prepared as follows: a 3-substituted-2-cyanoiminothiazolidine whose substituent is the $R^1$ group, which can be prepared according to the method described in Japanese Patent Kokai No. 48-91064, is reacted with hydrazine monohydrate in a solvent or without solvent, in the presence or absence of a catalyst to give the compound of Formula I wherein $R^3$ is other than an acetyl group. The resulting compound is reduced with zinc in a mixture of acetic anhydride and acetic acid to give the compound of Formula I wherein $R^3$ is an acetyl group. Examples of the solvent used in the reaction with hydrazine monohydrate are reaction-inert solvents such as water, methanol, ethanol, isopropanol, tetrahydrofuran and dioxane. Examples of the catalyst are metal salts containing a $Fe^{2+}$ ion, a $Fe^{3+}$ ion, a $Cu^+$ ion, a $Cu^{2+}$ ion and a $Co^{2+}$ ion which are used for autooxidation from mercaptane to disulfide. The reaction temperature is from 0° C. to the boiling point of the solvent used. The reaction time depends on the starting materials and the reaction temperature, but termination of the reaction can be governed by observing the exhaustion of the starting material by the use of thin layer silica gel chromatography.

The compounds of the present invention show the remarkable inhibiting activity of lipid peroxidation with low toxicity, therefore, they are useful as the therapeutic and preventive agents of arteriosclerotic diseases including myocardial and cerebral infarctions, liver diseases, pulmonary edema, skin diseases, eye diseases and the tissue injuries by post-ischemic reperfusion in myocardial or cerebral infarctions. For these purposes, these compounds can be administered orally or parenterally in a conventional dosage forms such as tablets, powders, pilles, capsules, granules, solutions, emulsions and injectionable solution, each of which can be prepared in accordance with ordinary pharmaceutical practices. In these preparations, there can be used ordinary additives such as fillers, binders, disintegrators, pH-regulators and solublizers.

The dosage of the compound of the present invention for a patient depends on the age of the patient, and the kind and conditions of the disease, but usually it is from 10 to 5000 mg in single or several doses per day.

The inhibition test result of lipid peroxidation of the representative compounds of the present invention is shown herein.

EXPERIMENT [INHIBITION TEST OF LIPID PEROXIDATION]

To the cerebral tissue collected from male Wister strain rats was added a four-fold volume of posphate buffer (pH 7.4), and the mixture was homogenized and centrifuged at 2300 rpm for 10 minutes to give a supernatant, which was then diluted to its four-fold volume with the same phosphate buffer as that used above. To 1 ml of the diluted solution was added the solution of the test drug (the compound of the present invention; and vitamin E as a control; the final concentration is 100 $\mu M$ or $5\mu M$) in 10 $\mu l$ of dimethyl sulfide. After incubation at 37° C. for 30 minutes, the formation amount of malondialdehyde, which was the secondary product of lipid peroxidation, was quantitated according to the thiobarbituric acid method, and the % inhibition were calculated as the formation amount in the group treated with dimethyl sulfoxide only being 100%. Results are shown in Table 1.

The Compound numbers in Table 1 correspond to those in the Examples described below.

TABLE 1

| Test drug | Inhibition (%) | |
|---|---|---|
| (Compound No.) | Dose 100 $\mu M$ | Dose 5 $\mu M$ |
| 6 | 55.7 | — |
| 7 | 96.0 | 31.4 |
| 13 | — | 51.1 |
| 14 | — | 49.2 |
| 17 | 100 | 22.2 |
| 18 | — | 71.7 |
| 19 | 100 | 21.3 |
| 20 | — | 35.2 |
| 22 | — | 36.6 |
| 23 | — | 48.1 |
| 24 | — | 41.6 |
| 25 | — | 51.8 |
| 29 | — | 70.8 |
| 30 | — | 85.8 |
| 33 | — | 35.6 |
| 34 | — | 55.8 |
| 37 | — | 31.4 |
| 38 | — | 56.8 |
| 39 | — | 56.3 |
| vitamin E | 30.5 | 12.6 |

The present invention is illustrated in more detail by the following examples.

EXAMPLE 1

To a suspension of 0.24 g of sodium hydride in 40 ml of N,N-dimethylformamide was added dropwise a solution of 1.27 g of 2-cyanoiminothiazolidine in 10 ml of N,N-dimethylformamide, and the mixture was stirred at room temperature for 30 minutes. After stirring, 1.27 g of benzyl chloride was added, and the mixture was stirred at temperature for 2 hours. After the reaction, the solvent was evaporated under reduced pressure, water was added to the residue, and the resulting crystals were then collected by filtration to give 1.84 g of 3-benzyl-2-cyanoiminothiazolidine.

m.p. 102°–103° C.

A mixture of 1.84 g of 3-benzyl-2-cyanoiminothiazolidine and 10 ml of hydrazine monohydrate was heated at reflux under an algon atmosphere for an hour. After the reaction, the solvent was evaporated under reduced pressure, and the residue was recrystallized from ethanol to give 2 g of 5-amino-3-[N-(2-mercaptoethyl)benzylamino]-1,2,4-triazole (Compound 1).

m.p. 189°–194° C.

Following a procedure similar to that of Example 1 using the corresponding starting material, there was obtained 5-Amino-3-[N-(2-mercaptoethyl)-2,4,6-trimethylbenzylamino]-1,2,4-triazole (Compound 2).

m.p. 173°–179° C.

EXAMPLE 2

To a mixture of 1.27 g of 2-cyanoiminothiazolidine well-known and 20 ml of methanol was added 0.3 ml of hydrazine monohydrate, and the mixture was stirred at room temperature for an hour. After the reaction, the solvent was evaporated under reduced pressure, and the residue was recrystallized from water to give 1.42 g of bis{2-[N-(5-amino-1,2,4-triazol-3-yl)amino]ethyl}disulfide (Compound 3).

m.p. 231°–233° C.

EXAMPLE 3

A mixture of 1.0 g of 5-amino-3-[N-(2-mercaptoethyl)benzylamino]-1,2,4-triazole, 20 ml of methanol and 5 mg of ferrous sulfate heptahydrate was stirred at room temperature for 16 hours. After the reaction, the resulting crystals were collected by filtration to give 0.9 g of bis{2-[N-benzyl-N-(5-amino-1,2,4-triazol-3-yl) amino]ethyl}disulfide (Compound 7).

m.p 200°–203° C.

Following a procedure similar to that of Example 2 or 3, there were obtained the following compounds listed in Table 2 (wherein the compounds obtained in Examples 2 and 3 also were indicated) from the corresponding starting materials.

TABLE 2

$$\underset{H_2N}{\overset{H}{\underset{N}{\nwarrow}}}\underset{N}{\overset{N}{\diagdown}}{\diagup}N-CH_2CH_2-S-S-CH_2CH_2-N\underset{R^1}{\diagup}\underset{N}{\overset{N}{\diagup}}\underset{NH_2}{\overset{H}{\nearrow}}$$

| Compound No. | R$^1$ | m.p. (°C.) |
|---|---|---|
| 3 | H | 231–233 |
| 4 | CH$_3$ | 206–208 |
| 5 | C$_2$H$_5$ | 162–165 |
| 6 | i-C$_3$H$_7$ | 157–158.5 |
| 7 | —CH$_2$—C$_6$H$_5$ | 200–203 |
| 8 | —CH$_2$—C$_6$H$_4$-F (meta) | 196–198 |
| 9 | —CH$_2$—C$_6$H$_4$—F (para) | 185–186 |

TABLE 2-continued

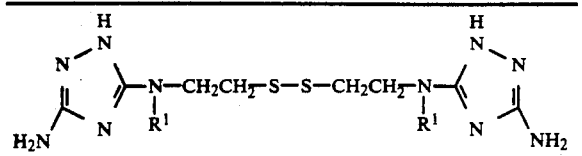

| Compound No. | R¹ | m.p. (°C.) |
|---|---|---|
| 10 | —CH₂—(2-Cl-C₆H₄) | 158–162 |
| 11 | —CH₂—(3-Cl-C₆H₄) | 190–191 |
| 12 | —CH₂—(4-Cl-C₆H₄) | 183–187 |
| 13 | —CH₂—(3-Br-C₆H₄) | 182–182.5 |
| 14 | —CH₂—(4-Br-C₆H₄) | 181–182 |
| 15 | —CH₂—(2-I-C₆H₄) | 132–134 |
| 16 | —CH₂—(3-OCH₃-C₆H₄) | 167.5–168.5 |
| 17 | —CH₂—(4-OCH₃-C₆H₄) | 130–133 |
| 18 | —CH₂—(4-OCH₂C₆H₅-C₆H₄) | 193.5–195.5 |
| 19 | —CH₂—(3-NO₂-C₆H₄) | 204–206 |
| 20 | —CH₂—(4-NO₂-C₆H₄) | 196–199 |
| 21 | —CH₂—(3-CN-C₆H₄) | note 1 |
| 22 | —CH₂—(3-CF₃-C₆H₄) | 172–174 |
| 23 | —CH₂—(3-CH₃-C₆H₄) | 181–184 |
| 24 | —CH₂—(2-CH₃-C₆H₄) | 212.5–213 |

TABLE 2-continued

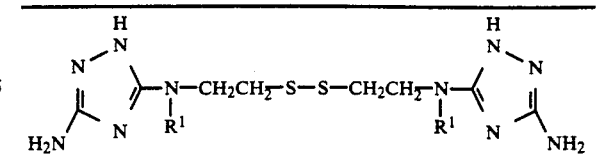

| Compound No. | R¹ | m.p. (°C.) |
|---|---|---|
| 25 | —CH₂—(4-CH₃-C₆H₄) | 200–201 |
| 26 | —CH₂—(2,4-(CH₃)₂-C₆H₃) | 120–123 |
| 27 | —CH₂—(2,3-(CH₃)₂-C₆H₃) | 204–206 |
| 28 | —CH₂—(2,6-(CH₃)₂-C₆H₃) | 191–194 |
| 29 | —CH₂—(3,4-(CH₃)₂-C₆H₃) | 233–235 |
| 30 | —CH₂—(2,4,6-(CH₃)₃-C₆H₂) | 241–246 |
| 31 | —CH₂—(4-C₂H₅-C₆H₄) | 197.5–199.5 |
| 32 | —CH₂—(4-i-C₃H₇-C₆H₄) | 198.5–200.5 |
| 33 | —CH₂—(4-t-C₄H₉-C₆H₄) | 199–202 |
| 34 | —CH₂—(4-C₆H₅-C₆H₄) | 206–209 |
| 35 | —CH₂—(2-NO₂-3-CH₃-C₆H₃) | 160–170 |
| 36 | —CH₂—(2-NO₂-4-CH₃-C₆H₃) | 142–146 |
| 37 | —CH₂—(2-NO₂-6-CH₃-C₆H₃) | 157.5–160 |
| 38 | —CH₂—(1-naphthyl) | 193–196 |

TABLE 2-continued

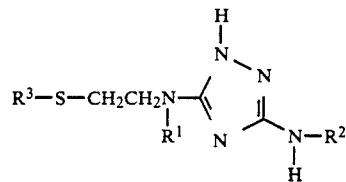

| Compound No. | R¹ | m.p. (°C.) |
|---|---|---|
| 39 | —CH₂—(2-naphthyl) | 214–218 |
| 40 | —CH₂—(9-anthryl) | 140–148 |

Note 1:
H-NMR (DMSD-d₆) 2.6–3.1 (4H, m), 3.2–3.8 (4H, m), 4.54 (4H, s), 5.1–6.1 (4H, m), 7.1–8.1 (8H, m)

EXAMPLE 4

To a mixture of 0.316 g of bis{2-[N-(5-amino-1,2,4-triazole-3-yl)amino]ethyl}disulfide and 0.98 g of an activated zinc powder which was washed with dilute hydrochloric acid was added a mixture of 25 ml of acetic anhydride and 5 ml of acetic acid under an argon atmosphere with ice-cooling, and the mixture was stirred for 45 minutes. After the reaction, the insolubles were removed by filtration, and the filtrate was evaporated under reduced pressure. The residue was purified by silica gel column chromatography [Eluent; ethyl acetate:hexane=1:1) and then recrystallized from a mixture of ethyl acetate and hexane to give 0.188 g of 5-acetamido-3-[N-(acetylthioethyl)amino]-1,2,4-triazole.

m.p. 127°–130° C.

Following a procedure similar to that of Example 4, the following compounds were prepared from the corresponding starting materials.

5-Acetamido-3-[N-methyl-N-(2-acetylthioethyl)-amino]-1,2,4-triazole
m.p. 96°–97° C.

5-Acetamido-3-[N-ethyl-N-(2-acetylthioethyl)-amino]-1,2,4-triazole
m.p. 109°–110.5° C.

5-Acetamido-3-[N-isopropyl-N-(2-acetylthioethyl-)amino]-1,2,4-triazole
m.p. 140°–142° C.

5-Acetamido-3-[N-benzyl-N-(2-acetylthioethyl)-amino]-1,2,4-triazole
m.p. 109°–110° C.

What is claimed is:

1. A triazole derivative represented by the formula

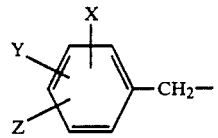

wherein R¹ is an acetyl group, a naphthylmethyl group, an anthrylmethyl group or a group of the formula

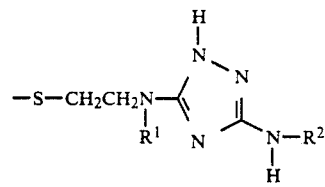

wherein X, Y and Z are the same or different and each a hydrogen atom, a halogen atom, a lower alkyl group having 1 to 4 carbon atoms, a lower alkoxy group having 1 to 4 carbon atoms, a hydroxyl group, a nitro group, a trifluoromethyl group, a cyano group or a benzyloxy group, and R² is a hydrogen atom or an acetyl group, and R³ is a hydrogen atom, an acetyl group or a group of the formula $$-S-CH_2CH_2N\underset{R^1}{\overset{|}{N}}\underset{\underset{H}{|}}{\overset{}{\underset{N}{\overset{H}{|}}}}\underset{N}{\overset{N}{\diagdown}}N-R^2$$

wherein R¹ and R² are as defined above.

2. 5-Amino-3-[N-(2-mercaptoethyl)benzylamino]-1,2,4-triazole.
3. 5-Amino-3-[N-(2-mercaptoethyl)-2,4,6-trimethylbenzylamino]-1,2,4-triazole.
4. Bis{2-[N-(5-amino-1,2,4-triazol-3-yl)-N-benzylamino]ethyl}disulfide.
5. Bis{2-[N-(5-amino-1,2,4-triazol-3-yl)-N-(3-bromobenzyl)amino]ethyl}disulfide.
6. Bis{2-[N-(5-amino-1,2,4-triazol-3-yl)-N-(4-benzyloxybenzyl)amino]ethyl}disulfide.
7. Bis{2-[N-(5-amino-1,2,4-triazol-3-yl)-N-(2,5-dimethylbenzyl)amino]ethyl}disulfide.
8. Bis{2-[N-(5-amino-1,2,4-triazol-3-yl)-N-(2,4,6-trimethylbenzyl)amino]ethyl}disulfide.
9. Bis{2-[N-(5-amino-1,2,4-triazol-3-yl)-N-(4-tert-butylbenzyl)amino]ethyl}disulfide.
10. Bis{2-[N-(5-amino-1,2,4-triazol-3-yl)-N-(α-naphthylmethyl)amino]ethyl}disulfide.
11. Bis{2-[N-(5-amino-1,2,4-triazol-3-yl)-N-(β-naphthylmethyl)amino]ethyl}disulfide.

* * * * *